(12) United States Patent
Kuribayashi et al.

(10) Patent No.: US 8,097,262 B2
(45) Date of Patent: Jan. 17, 2012

(54) GEL TYPE ENTERAL NUTRIENT

(75) Inventors: Minoru Kuribayashi, Hanamaki (JP); Yasunori Kogami, Hanamaki (JP)

(73) Assignee: En Otsuka Pharmaceutical Co., Ltd., Hanamaki-Shi (JP)

( * ) Notice: Subject to any disclaimer, the term of this patent is extended or adjusted under 35 U.S.C. 154(b) by 63 days.

(21) Appl. No.: 12/441,063

(22) PCT Filed: Aug. 31, 2007

(86) PCT No.: PCT/JP2007/000941
§ 371 (c)(1),
(2), (4) Date: Apr. 10, 2009

(87) PCT Pub. No.: WO2008/032432
PCT Pub. Date: Mar. 20, 2008

(65) Prior Publication Data
US 2010/0040739 A1  Feb. 18, 2010

(30) Foreign Application Priority Data
Sep. 13, 2006 (JP) ................................. 2006-247460

(51) Int. Cl.
| | |
|---|---|
| A61K 9/00 | (2006.01) |
| A61K 36/02 | (2006.01) |
| A61K 36/48 | (2006.01) |
| A61K 33/06 | (2006.01) |
| A61K 38/00 | (2006.01) |
| A61K 31/70 | (2006.01) |
| A61K 31/715 | (2006.01) |
| A61K 47/00 | (2006.01) |
| A61K 31/734 | (2006.01) |
| A61K 31/729 | (2006.01) |
| A61K 47/36 | (2006.01) |
| A23L 1/0532 | (2006.01) |
| A23L 1/30 | (2006.01) |
| A23L 1/09 | (2006.01) |
| A23L 1/236 | (2006.01) |
| A23L 1/05 | (2006.01) |
| A23B 7/005 | (2006.01) |
| B65D 85/00 | (2006.01) |
| A61P 3/02 | (2006.01) |
| A61K 35/20 | (2006.01) |
| A23L 3/005 | (2006.01) |
| A23L 1/32 | (2006.01) |
| A23K 1/175 | (2006.01) |

(52) U.S. Cl. ................... 424/400; 424/195.17; 424/757; 424/682; 424/535; 424/439; 426/648; 426/74; 426/106; 426/575; 426/800; 426/72; 426/658; 426/656; 426/654; 426/810; 514/5.5; 514/58; 514/779; 514/878; 514/944; 514/777; 514/23; 514/53; 514/1.1; 514/773

(58) Field of Classification Search ...................... 426/74, 426/575, 106
See application file for complete search history.

(56) References Cited

U.S. PATENT DOCUMENTS
| | | | | |
|---|---|---|---|---|
| 4,769,261 | A | * | 9/1988 | Hazelton et al. ............. 428/35.3 |
| 4,956,193 | A | | 9/1990 | Cain et al. |
| 5,232,733 | A | * | 8/1993 | Resmer ......................... 426/590 |
| 6,638,540 | B2 | * | 10/2003 | Muhlbauer ................... 424/725 |
| 2003/0104033 | A1 | * | 6/2003 | Lai et al. ....................... 424/439 |
| 2004/0197381 | A1 | * | 10/2004 | Kanie ............................ 424/439 |

FOREIGN PATENT DOCUMENTS
| | | |
|---|---|---|
| EP | 0419885 A1 | 4/1991 |
| EP | 1364585 A1 | 11/2003 |
| JP | 4-501511 A | 3/1992 |
| JP | 2000-169396 A | 6/2000 |
| JP | 2000-169397 A | 6/2000 |
| JP | 2000-217544 A | 8/2000 |
| JP | 2001-316278 A | 11/2001 |
| JP | 2003-201230 A | 7/2003 |
| JP | 2004-91485 A | 3/2004 |
| JP | 2006-182767 A | 7/2006 |
| KR | 10-2005-0060630 | 6/2005 |

OTHER PUBLICATIONS

Wikipedia (on-line encyclopedia), Reference Daily Intake, [Retrieved on Oct. 9, 2010] Retrieved from the internet < URL: http://en.wikipedia.org/wiki/Reference_Daily_Intake>, 3 pages.*
USDA National Agricultural Library, Food and Nutrition Information Center, Dietary Reference Intakes (DRIs): Recommended Dietary Allowances and Adequate Intakes, Vitamins/Elements, Food and Nutrition Board, Institute of Medicine, National Academies [downloaded Feb. 17, 2011] [Retrieved from internet <URL: http://iom.edu/Activities/Nutrition/SummaryDRIs/~/media/Files/Activity%20Files/Nutrition/DRIs/RDA%20and%20Als_VItamin%20and %20Elements.pdf>], 3 pages.*
JP 2006-182767 (macine translation), 19 pages.*

(Continued)

Primary Examiner — Ernst Arnold
Assistant Examiner — Miriam A Levin
(74) Attorney, Agent, or Firm — Birch, Stewart, Kolasch & Birch, LLP

(57) ABSTRACT

An enteral nutrient gel that is excellent at maintaining its solid matter (gel) form in the stomach, does not readily disintegrate or dissolve with a change in pH, is stable in its physical properties even during long-term storage, and can be passed through a feeding tube. The enteral nutrient gel contains agar, alginic acid and/or a salt thereof, soybean protein or a hydrolysate thereof, calcium, magnesium, dextrin, and, optionally, an oligosaccharide, a disaccharide and/or a monosaccharide. A solid composition containing 8 to 30 wt % protein, 2 to 25 wt % fats, and 40 to 70 wt % dextrin is used in preparing the enteral nutrient gel.

5 Claims, No Drawings

OTHER PUBLICATIONS

International Preliminary Report on Patentability (Chapter I of the Patent Cooperation Treaty) for PCT/JP2007/00941, issued Mar. 17, 2009. (English Translation) [Downloaded Aug. 11, 2011] [Retrieved from internet—<URL: http://www.wipo.int/patentscope/search/en/detail.jsf?docId=WO2008032432&recNum=1&tab=PCTDocuments&maxRec=1&office=&prevFilter=&sortOption=&queryString=FP%3A%28+PCT%2FJP2007%2F00941%29 >] (5 pages).*

Written Opinion of the International Searching Authority (PCT Rule 4.3 bis 1) for PCT/JP2007/000941, international filed date Aug. 31, 2007 (English Translation) [Downloaded Aug. 11, 2011] [Retrieved from internet—<URL: http://www.wipo.int/patentscope/search/en/detail.jsf?docId=WO2008032432&recNum=1&tab=PCTDocuments&maxRec=1&office=&prevFilter=&sortOption=&queryString=FP%3A%28+PCT%2FJP2007%2F00941%29 >] (4 pages).*

Applewhite TH (ed) (1989) Proceedings of the World Congress on Vegetable Protein Utilization in Human Food and Animal Feedstuffs. Congress held in Singapore in Oct. 1988. American Oil Chemists Soc., Champaign, Illinois, p. 349.

Opposition in European Patent No. 2,062,598 dated May 2, 2011.

Supplementary European Search Report for European Patent Application No. 07805796 dated Sep. 14, 2009.

Ishii et al , "Tainetsusei Alginic Acid Jelly no Tokusei Yoto," Japan Food Science, vol. 27, No. 7, pp. 35-41, 1988.

* cited by examiner

GEL TYPE ENTERAL NUTRIENT

TECHNICAL FIELD

The present invention relates to a gel-type enteral nutrient which is used as an enteral nutrient or fluid diet in the medical field, has a good tube passing property for feeding tubes while being in solid form (gel), indicates the effect of preventing gastro-esophageal reflux after administration since the solid (gel) does not easily dissolved or disintegrated in a stomach and maintains its shape, in addition prevents gastro-esophageal reflux due to separation of water since the nutrient exhibits a very small change in properties such as an increase in separation of water during distribution and storage, and can be subjected to thermal sterilization such as retort sterilization.

BACKGROUND ART

In recent years, along with the advent of an aging society, the number of patients who are administered a nutrient through a feeding tube as a means of administering the nutrient to old persons for whom oral administration is difficult has increased. In particular, since percutaneous endoscopic gastrostomy (PEG) which can easily form a gastric fistula using an endoscope has been developed, PEG has been widely used as a safe and effective nutrient administration means. However, some problems on nutritional management for PEG patients have been reported. For example, gastro-esophageal reflux, enteral nutrient leakage, diarrhea, or the like can be given. These conditions may often cause a serious complication that threatens the life of patients, such as aspiration pneumonia, infectious diseases, or dehydration. It has been noticeably reported that the above conditions are considered to occur because the enteral nutrient is a non-physiologic liquid, and as a countermeasure thereagainst it is effective to solidify the liquid nutrient or adjust the viscosity of the liquid nutrient.

Several inventions have been conceived based on the above finding. For example, a semi-solid enteral nutrient that has a hardness approximately equal to that of pudding or steamed egg hotchpotch by adding agar or a whole egg as a semi-solidifying agent has been disclosed (see Patent Documents 1 and 2, for example). A food for preventing dumping which comprises a thickener selected from low-methoxyl pectin, alginic acid, and carrageenan has been disclosed (see Patent Document 3, for example). This food is injected into a stomach through a tube before and after administration of a nutrient to form a solid in the stomach. This prevents a rapid inflow of the nutrient into the intestine to prevent transient hyperglycemia (dumping syndrome). In addition, a tube-feeding nutrient which can prevent gastro-esophageal reflux and dumping syndrome, can be administered at a desired viscosity within a short time without uncomfortably affecting a patient and a nurse, and can be prepared safely and easily, has been disclosed (see Patent Document 4, for example). As a thickener used in the tube-feeding nutrient guar gum, carrageenan, carboxymethyl cellulose, xanthan gum, chitin, chitosan, or the like can be exemplified. Gelatin, locust bean gum, gellan gum, glucomannan, curdlan, or the like has been generally used for a jelly food and the like in addition to the above-mentioned thickener and gelling agent.

However, these conventional technologies have problems in that even if the products are solid, some solid products are dissolved or disintegrated due to the gastric pH and gastric peristalsis to disappear the shape thereof, solid (gel) forming capability is reduced or lost during retort sterilization due to lack of heat resistance, the solid products must be pressed into by strong force during PEG tube administration using a syringe or the like because the solid increases the viscosity and the tube sometimes may be clogged, or the products may change in form due to separation of water or the like during storage. For example, the enteral nutrient solidified using agar or a whole egg (Patent Documents 1 and 2) exhibits fragile nature in a stomach and is discretely disintegrated and thus gastro-esophageal reflux cannot be prevented sufficiently. In particular, water is separated in the enteral nutrient solidified using agar or a whole egg (Patent Documents 1 and 2) during distribution or long-term storage. There are problems that when the enteral nutrient in which water has been separated is administered to a patient, gastro-esophageal reflux, nutrient leakage, or the like occurs.

A nutrient solidified using the food disclosed in Patent Document 3 can maintain its form in an acidic stomach. However, when the gastric pH has changed due to the inflow of a neutral liquid such as an intestinal juice or the like, the nutrient is easily dissolved or disintegrated to acquire flowability and thus the risk of gastro-esophageal reflux may occur. Patent Document 4 describes only a viscous tube-feeding nutrient, but is silent about the solid form-maintaining capability in a stomach, resistance against thermal sterilization, and a change in form during storage of the product due to separation of water or the like. Therefore, a drug product that can solve the above-described problems cannot be prepared.

From these circumstances, in the above-mentioned conventional technologies, a gel-type nutrient which has excellent solid form-maintaining capability in a stomach, exhibits a property of easily passing through a tube, shows a very little change in shape during storage of the product due to separation of water or the like, and has heat resistance tolerating retort sterilization could not be produced. In particular, there is a big problem that water is separated in an enteral nutrient during distribution or long-term storage, and the enteral nutrient in which water has been separated occurs gastro-esophageal reflux, or nutrient leakage when the nutrient is administered to a patient.

Patent Document 1: JP-A-2003-201230
Patent Document 2: JP-A-2004-26844
Patent Document 3: Japanese Patent No. 3140426
Patent Document 4: JP-A-2004-217531

DISCLOSURE OF THE INVENTION

Problems to be Solved by the Invention

In view of the problems of the conventional technologies mentioned above, an object of the present invention is to provide a gel-type enteral nutrient that has excellent solid (gel) form-maintaining capability in a stomach, is not easily dissolved or disintegrated even if a change in pH has occurred due to the backward flow of an intestinal juice or the like, has the physical property that the nutrient can be administered through a PEG tube with a appropriate force using a syringe or the like, exhibits a very little change in physical properties of separation of water or the like during long-term storage of the product, and has heat resistance capable of subjecting to retort sterilization. More particularly, an object of the present invention is to provide a gel-type enteral nutrient that is administered to PEG patients and the like through a tube, does not cause gastro-esophageal reflux, nutrient leakage and the like, does not clog a tube during administration, has been subjected to retort sterilization, and does not change until the level of question in qualities of separation of water or the like during long-term storage.

Means for Solving the Problems

The inventors of the present invention conducted extensive studies, and found to be able to provide a gel-type enteral nutrient that has excellent solid (gel) form-maintaining capability in a stomach, has a property easily passing through a PEG tube, and exhibits a very little change in separation of water or the like during long-term storage of the product by comprising such component and composition as gel-type enteral nutrient which is blended with agar, alginic acid and/or salt thereof, and a soybean protein as a nitrogen source.

Effect of the Invention

According to the present invention, a gel-type enteral nutrient which possesses the four excellent effects in the same time, which are described below, can be provided by blending with three components of agar, alginic acid and/or salt thereof, and a soybean protein or hydrolysate thereof, in specified amounts. That is, the gel-type enteral nutrient (a) has excellent solid (gel) form-maintaining capability in a stomach and thus exhibits a preventive effect on gastro-esophageal reflux after administration, (b) has a property easily passing through a PEG tube in spite of gel, (c) exhibits a very little change in separation of water or the like during distribution and storage, and (d) can be subjected to retort sterilization.

In particular, the inventors firstly found that even a conventional gelled nutrient possesses problems to causes gastro-esophageal reflux, nutrient leakage, and the like due to separation of water during distribution and storage (corresponding to the effect of (c)). Therefore, any invention that intends to solve such a problem has not been proposed heretofore.

BEST MODE FOR CARRYING OUT THE INVENTION

The formation of the gel-type enteral nutrient according to the present invention was conceived as described below. The inventors confirmed that problems occur when employing the formations of a conventional gel nutrient, and conducted studies on these formations. Main problems which are revealed in the above studies on the conventional technology are listed below.

(1) Enteral nutrients solidified using agar or a whole egg (Patent Documents 1 and 2) occur a significant water-separation phenomenon during storage or due to impact such as vibration or falling, and thus the preventive effects for the gastro-esophageal reflux are reduced or lost.

(2) An enteral nutrient solidified using a polysaccharide such as pectin (Patent Document 3) or carrageenan has low resistance against thermal sterilization. Therefore, significant separation of water occurs during retort sterilization.

(3) An enteral nutrient solidified by forming the structure of with an ionic bond using pectin or carrageenan has a disintegrating or dissolving property depending on the change in pH and loses solid shape-maintaining capability in a stomach.

(4) An enteral nutrient solidified using a viscous thickener and a gelling agent, such as guar gum, pectin or the like exhibits a remarkably poor property passing through a PEG tube and very poor adhesion property.

By taking into consideration the above-mentioned problems, the inventors conducted extensive studies on the types of a thickener and a gelling agent and the like, and combination and amounts thereof, and confirmed by examination. Specifically, the inventors searched for (1) a gelling agent that produces a gel-type enteral nutrient that shows a high gel strength (hardness) with a small amount of addition. The inventors then searched for a combination of gelling agents that ensures that the resulting gel-type enteral nutrient (2) has excellent shape-maintaining capability in a stomach, (3) separates water in a small amount, and (4) easily passes through a tube. The inventors further searched for a combination of gelling agents that ensures that the resulting gel-type enteral nutrient (5) has heat resistance, (6) shows long-term storage stability, and (7) rarely shows a deterioration in quality during distribution. As a result, the inventors found that a nutrient blending alginic acids to agar, in combination with any gelling agents, satisfies all of the above-mentioned items. For example, agar (1) is gelled with a small amount of gelling agent, and (4) is a material which exhibits a property easily passing through a tube. However, agar has disadvantages such as fragile property, easily disintegrating in a stomach, and separating a large amount of water. The inventors found that these disadvantages can be overcome by combining with alginic acids.

As a result of these studies, the inventors accomplished the present invention. Specifically, the inventors found that a gel-type enteral nutrient that has excellent solid (gel) form-maintaining capability in a stomach, is not easily dissolved or disintegrated even if pH is changed, rarely shows a change in properties of separation of water or the like during long-term storage, can be subjected to thermal sterilization, and easily passes through a feeding tube can be prepared by blending agar and alginic acid and/or salt thereof. The inventors also found that the above-mentioned characteristics are further improved by adding a soybean protein or hydrolysate thereof as a nitrogen source. Particularly, it is a big feature of the present invention that gastro-esophageal reflux, nutrient leakage, or the like due to separation of water can be prevented, since a change in properties such as increase in separation of water during distribution or storage can be suppressed.

The gel-type enteral nutrient according to the present invention has the following constitution.

(1) The gel-type enteral nutrient comprises agar and alginic acid and/or salt thereof.

(2) The gel-type enteral nutrient contains nutritional elements necessary for a living body, and particularly contains a soybean protein as a nitrogen source.

Since the gel-type enteral nutrient according to the present invention has the above constitution, the nutrient has excellent characteristics that cannot be obtained by conventional technologies in terms of properties and long-term storage. Specifically, the gel-type enteral nutrient has excellent solid (gel) form-maintaining capability in a stomach without being easily dissolved or disintegrated even if pH is changed, rarely shows a change in properties of separation of water or the like during long-term storage, can be subjected to thermal sterilization, and easily passes through a feeding tube. Among the above components of the present invention, agar relatively easily forms a solid without being affected by the type and amount of nutritional elements contained in the enteral nutrient, and exhibits a good gel property that easily passes through a tube. On the other hand, agar has properties of easily separating water and being fragile. Therefore, agar cannot be stored for a long period of time. This makes it difficult to utilize agar for an enteral nutrient product that is commercially distributed. Moreover, agar has disadvantage that it cannot maintain its solid form under acidic conditions such as in a stomach, and is easily disintegrated discretely. The inventors searched for a composition that can overcome the above-mentioned disadvantages of the nutrient using agar, improve solid (gel) form-maintaining capability in a stomach, and can prevent separation of water during long-term storage. As a result, the inventors found that the above-mentioned disadvantages can be improved by combining agar with alginic acid and/or salt thereof. Meanwhile, a nutrient solidified using only alginic acid or salt thereof alone has solid form-maintaining capability in a stomach, but becomes easily flowable due to a change in pH. Moreover, such a nutrient has disadvantage that problem may arise in capability of passing through a tube due to high viscosity. The inventors found that the disadvantages of agar and the disadvantages of alginic acid and/or salt thereof can be compensated for by combining agar with alginic acid and/or salt thereof. These findings have led to completion of the present invention. The inventors studied using carrageenan, gellan gum, glucomannan, pectin, locust bean gum, and the like that are generally used as a gelling agent in a research for combination of agar with a thickener and a gelling agent other than alginic acid and/or salt thereof. However, a gel-type enteral nutrient having all features of the present invention could not be obtained.

The combination of agar and alginic acid and/or salt thereof according to the present invention has distinctive effect that separation of water is particularly low during distribution and storage. The reasons resulted in the best combination may include as follows.

(1) Hydrogen bonds in a molecular chain and between molecular chains of agar produced by a change in temperature (cooling after heating) form a three-dimensional structure in the gelation of agar. On the other hand, alginic acids forms a three-dimensional structure due to gelation according to chelating (ionic bonds) with a mineral such as calcium or a metal salt thereof. Therefore, a hybrid gel having a novel function can be produced using the materials that differ in gelling mechanism.

(2) The polysaccharide that forms alginic acid is linear and is not branched, differing from other gelling agents. Therefore, alginic acid forms a hybrid mesh structure with agar without inhibiting the three-dimensional structure formed by the hydrogen bonds of agar by tangling both materials, thereby bringing a novel function that has not ever been recognized.

(3) Since the structure of an agar gel is formed by a number of intramolecular and intermolecular hydrogen bonds, the number of hydrogen-bonding sites (e.g., hydroxyl group) between the agar molecules and water molecules is small. Therefore, water is hardly held in the gel but easily separated. On the other hand, since alginic acids forms a structure due to gelation according to chelating (ionic bonds) with a mineral such as calcium or a metal salt thereof, many hydrogen-bonding sites connect to water molecules. Therefore, water is held in the gel, and the effect suppressing the separation of water may be recognized. Specifically, these hybrid gels effectively utilizes the water-holding capability of alginic acid.

(4) Although agar lacks heat resistance, an alginic acid gel has excellent heat resistance. In the agar-alginic acid hybrid gel, the heat resistance of the alginic acid gel reinforces and maintains the gel structure to suppress disintegration of the gel structure.

(5) Agar forms a hard and fragile gel. On the other hand, alginic acids forms a relatively elastic gel. Alginic acids sufficiently maintains the gelation strength in gastric acid. Therefore, the hybrid gel keeps the properties of alginic acid, improves form-maintaining capability in a stomach, and exhibits an effect of preventing disintegration during distribution due to elasticity.

(6) On the other hand, since alginic acids does not basically change the gelation structure of agar, inherent properties of agar such as excellent tube-passing properties and the like are maintained.

The inventors further conducted studies, and found that addition of a soybean protein as a nitrogen source to the gel-type enteral nutrient that contains agar and alginic acid and/or salt thereof remarkably improves the above-mentioned features, and a more preferable gel-type enteral nutrient can be thus prepared.

The type of agar used in the present invention is not particularly limited. Agar or powdered agar described in the Japanese Pharmacopoeia, powdered agar, rod agar stick, instantly soluble agar, or the like may be used. The types of alginic acid and salt thereof are also not particularly limited. Alginic acid and salt thereof specified as a pharmaceutical excipients or food additives may be used. The type of alginate is not particularly limited. Sodium alginate, calcium alginate, or the like may be used.

The raw materials added to the enteral nutrient are also not particularly limited. Nutritional elements necessary for a living body may be added. The features of the present invention can be maximized by using a soybean protein or hydrolysate thereof as a nitrogen source. The type of soybean protein is not particularly limited. Soymilk, a concentrated soybean protein, a separated soybean protein, a soybean peptide, or the like may be used. The amount of soybean protein is not particularly limited. It is sufficient to add the soybean protein in the amount as usually blended, preferably in a range of 0.5 to 4.4 g/100 ml in order to achieve the features of the present invention. Since the soybean protein is modified by heating to form a gel per se due to the function of the soybean protein or hydrolysate thereof, the soybean protein is thought to have a synergistic effect on the gelation of agar and alginic acid. Since the soybean protein can interact with both bonding schemes of agar that forms a gel via hydrogen bonds and alginic acid that forms a gel via bonds with calcium or magnesium, the soybean protein may be estimated to crosslink the molecules of agar and alginic acid and to change the gel characteristics to a large extent, thereby contributing the storage stability of the gel and the like. It is to use the soybean protein is not necessarily used as all nitrogen source. For example, commonly-used protein such as a milk protein, milk casein, caseinate, or the like may be appropriately used as the nitrogen source in combination with the soybean protein.

The amounts of agar and alginic acids added to the nutrient are not particularly limited. The addition amounts of agar and alginic into the nutrient acid are appropriately adjusted corresponding to the concentration of the nutrient and the addition amount of soybean protein. If the amounts of agar and alginic acid are too small, a gel is not formed. If the amounts of agar and alginic acid are too large, the resulting gel becomes hard and a problem on a passing property through a tube may occur. It is preferable to add agar in an amount of 0.05 to 0.5% and add alginic acid and salt thereof in a total amount of 0.02 to 0.45% based on the enteral nutrient product because the features of the present invention may be sufficiently achieved.

The solid content of the enteral nutrient is not particularly limited. If the solid content of the enteral nutrient is too low, a large amount of nutrient must be administered when nutritional elements required for a day are administered. This imposes a burden on the patient. If the solid content of the enteral nutrient is too high, the content of water is lacked, the patient may then dangerously suffer from dehydration. In this case, it is necessary to supply water. since gastro-esophageal reflux may dangerously occur even when supplying water, a solid material such as a jelly must be administered to the patient, and it is vexatiously complicated. In the present invention, the enteral nutrient having any solid content can be gelated by appropriately adjusting the amounts of agar and alginic acid. The solid content of the enteral nutrient is preferably 0.5 to 2 kcal/100 g. In this case, a gel-type enteral nutrient having the best physical properties and storage stability can be prepared.

In the present invention, calcium and magnesium contained in the nutrient affect the properties of the solid (gel). The content of these minerals is preferably 30 to 100 mg/100 ml as calcium, and 15 to 50 mg/100 ml as magnesium. If the content of calcium or magnesium is lower than the above ranges, the gel shape-maintaining capability decreases. If the content is higher than the above ranges, a heterogeneous gel is formed.

A carbohydrate added to the nutrient according to the present invention is involved in gelation itself as well as starch, and may affect the properties of the gel-type nutrient such as viscosity or the like. Therefore, it is preferable to appropriately add and use a dextrin, an oligosaccharide, a disaccharide such as sucrose, and/or a monosaccharide such as glucose. When the solid content of the nutrient is low and the amounts of agar and alginic acid are large, it is preferable to use dextrin and saccharide with low-molecular-weight that have a high decomposition rate. When the solid content of the nutrient is high and the amounts of agar and alginic acid are small, it is preferable to use dextrin with a low decomposition rate. Removal of water during long-term storage may thereby be suppressed. In this case, it is preferable to appropriately add and use dextrins and low-molecular-weight saccharides that differ in decomposition rate.

Other nutritional elements than the elements added to the nutrient as described above are not particularly limited, and any raw materials may be used. As fats used in the present invention, for example natural fats such as soybean oil, corn oil, palm oil, safflower oil, fish oil, and the like, and a medium-chain triglyceride (MCT) having about 6 to 12 carbon atoms, and the like may be used, but it is not limited thereto. As vitamins and minerals used in the present invention, various trace nutritional element components, trace metals, and the like may be used.

A method of producing the gel-type enteral nutrient according to the present invention is not particularly limited. For example, a nitrogen source such as a protein, a carbohydrate, vitamins, minerals, fats, and an emulsifying agent are added to water, and a liquid enteral nutrient is prepared by conventional procedure, for example emulsifying the mixture using a homogenizer, and so on. A solution in which agar and alginic acids are previously dissolved with heating is then added to the enteral nutrient and mixed. A pouch such as an aluminum pouch, a soft bag, or the like is filled with the enteral nutrient, and is then subjected to thermal sterilization such as retort sterilization. Especially, the step of adding the solution of agar and alginic acid is not limited, but it is preferable to add the solution of agar and alginic acid before emulsifying the fats using a high-pressure homogenizer because agar and alginic acid are homogenously dispersed, and a gel-type enteral nutrient having a uniform color tone and properties can be thus prepared. After adding the solution of agar and alginic acids, the subsequent homogenization or filling step is carried out prior to cooling and gelling the enteral nutrient.

Since the gel-type nutrient thus prepared has form-maintaining capability in product state or in a stomach after administration, shows separation of water during long-term storage to only a small extent, and has certain degree of vibration resistance during distribution, a quality problem is not caused even though the gel-type nutrient is filled into a pouch such as an aluminum pouch or a soft bag. When a pouch provided with an outlet spout is filled with the gel-type nutrient according to the present invention, the gel-type enteral nutrient can be easily discharged by pressing the pouch. The spout is connected to a feeding tube such as PEG or the like, and the gel-type enteral nutrient can be easily administered to the patient by pressing the pouch with the hand or a compression tool.

A solidified nutrient prepared using conventional technology may remarkably decreases in passing property through a PEG tube due to high viscosity, the tube may be thereby clogged. In this case, the tube must be replaced by another tube, and the replacement inflicts undue pain on the patient. On the other hand, the gel-type enteral nutrient according to the present invention can be used safely, because there is no trouble caused by clogging the PEG tube which is exhibited in conventional solid-type enteral nutrients having high viscosity.

Since the gel-type enteral nutrient according to the present invention rarely shows a deterioration in quality such as separation of water when distributed in usual commodity form or stored for a long period of time, a sterilized gel-type enteral nutrient that can prevent gastro-esophageal reflux can be supplied practically.

The composition of nutritional elements in the enteral nutrient according to the present invention is not particularly limited insofar as the intended purpose of nutrition support and nutrition management can be achieved. the solid composition may be adjusted the blending ratio, in a case preparing a general gel-type enteral nutrient which is widely used, so that the content of the nitrogen represented as a protein is 8 to 30 wt %, the content of fats is 2 to 25 wt %, and the content of the carbohydrate is 40 to 70 wt %.

The administration form of the gel-type enteral nutrient according to the present invention is not particularly limited. The gel-type enteral nutrient may be administered by oral administration in addition to enteral administration through a PEG tube or the like.

In the following, the present invention is concretely explained by way of examples and the effects of the present invention is clearly described by way of comparative examples. However, the present invention should not be limited to the following examples.

When evaluating the properties that indicate the characteristics of the present invention, the following tests were conducted. The passing property through a tube was evaluated as follows. A 50 ml catheter chip syringe (manufactured by Terumo Corporation) was charged with about 50 g of a solid sample. A 20 Fr. PEG tube (Bard Ponsky N. B. R. catheter: manufactured by Medicon, Inc.) was connected to the syringe. The sample was discharged from the syringe at 50 g/15 sec using a compression testing machine (SV-55C: manufactured by Imada Seisakusho Co., Ltd.) to measure the pressing force (measurement temperature: 20° C.). On this occasion, the pressing force that the sample could be easily discharged with the hand is assumed 40 N or less. The water separation rate was determined as follows. About 50 g of a solid sample was placed on a 50-mesh sieve, and allowed to stand at 20° C. for 30 minutes. The amount of liquid (amount of separated water) that passed through the sieve was measured. The water separation rate was calculated from the ratio of the amount of separated water to the amount of the sample. On this occasion, the allowable range of the water separation rate was 5% or less as normal at which significant separation of water was not observed. The solid (gel) form-maintaining capability in a stomach was determined as follows. The paddle method in the elution test described in the Japanese Pharmacopoeia (15th revised edition) was used. the first solution (pH: 1.2) in the elution test was used as artificial gastric juice equivalent. The solid was added to the first solution, and the mixture was stirred for 60 minutes. The residual solid content was calculated from the residue obtained by filtration through a 50-mesh sieve. The solubility in an intestinal juice was evaluated as follows. The second solution (pH: 6.8) in the elution test was similarly used as artificial intestinal juice equivalent. The solid was added to the second solution, and the mixture was stirred for 60 minutes. The residual solid content was calculated from the residue obtained by filtration through a 50-mesh sieve. A test using a rat was also conducted to evaluate the solid (gel) shape-maintaining capability in a stomach. Specifically, about 2.2 g of a solid sample (about 10 g per kg of rat) was orally administered forcibly with a single dose to an SD rat (male, 8 weeks old) that was food-deprived overnight using a gastric tube for a rat. The contents of the stomach of the rat were taken out after 60 minutes, and the residual solid amount in the contents was measured. The ratio of the solid in the stomach to the dosage was calculated.

The long-term storage stability of the product was evaluated as follows. The product was stored in an incubator at a temperature of 25° C. and a humidity of 60% for 12 months, and changes in properties, pressing force, water separation rate, and the like were examined. The vibration/drop resistance was evaluated as follows. An aluminum pouch was filled with 200 g of the product, and packed in a common corrugated carton. The vibration/drop resistance was evaluated in accordance with the JIS Z 0200 test. Specifically, the vibration test was conducted under the following conditions: vibration direction: vertical sweep, frequency: 5 to 50 Hz, acceleration: ±0.75 G, sweep time: 300 seconds, and vibration time: 60 minutes. In the drop test, the sample was evaluated by dropping 10 times from a height of 60 cm. These tests were conducted at room temperature (20° C.). The appearance and the water separation rate were measured and adopted as evaluation item. Each test was repeated three times, and the average value was calculated.

In the above tests the properties (appearance) of the sample were evaluated by visually observing the items such as an uniformity and change in color tone, flavor, water separation condition, form-maintaining capability, flowability, and the like. The properties of the sample were evaluated by three observers, and the average value of these evaluations was adopted for overall evaluation.

EXAMPLE 1

A gel-type enteral nutrient with a solid content of 1.0 kcal/g was prepared by mixing the nutritional components in the blending amounts shown in Table 1. Specifically, a soybean protein was added to water first, and then dispersed at 70° C. using a TK homogenizer (manufactured by Tokushu Kika Kogyo Co., Ltd.). After the addition of fats containing an emulsifying agent, caseinate, dextrin, minerals, and vitamins to the dispersion liquid, an agar solution in which agar was dissolved with heating and an alginic acid solution in which alginic acid was dissolved in water using sodium citrate as a solubilization agent were then added to the mixture. After that, the mixture was emulsified using a high-pressure homogenizer without cooling at the temperature as is, thereby preparing an enteral nutrient according to the present invention that contained agar and alginic acids. 200 g of the enteral nutrient as obtained above was filled into an aluminum pouch, and the pouch was then subjected to retort sterilization at 121° C. for 15 minutes to obtain a product.

Comparative Example 1

The nutritional components shown in Table 1 were mixed in accordance with the method described in Patent Documents 1 and 2 to prepare an enteral nutrient with a solid content of 1.0 kcal/g which was added agar alone. Specifically, the enteral nutrient was prepared in the same manner as in Example 1, except that the alginic acid solution was not added and only agar solution was added.

Comparative Example 2

An enteral nutrient with a solid content of 1.0 kcal/g was prepared by adding low-methoxyl pectin according to the method described in Patent Document 3. Specifically, the enteral nutrient was prepared in the same manner as in Example 1, except that low-methoxyl pectin was added instead of the agar solution and the alginic acid solution.

TABLE 1

| | Blending amount | | |
|---|---|---|---|
| Component | Example 1 | Comparative Example 1 | Comparative Example 2 |
| Dextrin | 16.16 g | 16.16 g | 16.16 g |
| Soybean protein isolate | 1.67 g | 1.67 g | 1.67 g |
| Milk casein | 3.40 g | 3.40 g | 3.40 g |
| Fat (containing emulsifying agent) | 2.230 g | 2.230 g | 2.230 g |
| Calcium chloride | 117.6 mg | 117.6 mg | 117.6 mg |
| Calcium citrate | 39.5 mg | 39.5 mg | 39.5 mg |
| Magnesium chloride | 155.5 mg | 155.5 mg | 155.5 mg |
| Other minerals | 477.8 mg | 477.8 mg | 477.8 mg |
| Vitamins | 38.5 mg | 38.5 mg | 38.5 mg |
| Agar | 0.25 g | 0.50 g | — |
| Alginic acid | 0.25 g | — | — |
| Low methoxyl pectin | — | — | 100 g |
| Water | 75.2 g | 75.2 g | 74.7 g |
| Total | 100 ml | 100 ml | 100 ml |

Test Example 1

Regarding the enteral nutrient preparations of Example 1 and Comparative Examples 1 and 2, a quality test, a long-term storage test, a vibration/drop test, a disintegration/elution test using artificial gastric juice and artificial intestinal juice, and a gel formation/shape-maintaining test in a stomach using a rat were conducted and compared.

The results are shown in Table 2.

TABLE 2

| Test | Sample | Evaluation item | Result Example 1 | Result Comparative Example 1 | Result Comparative Example 2 |
|---|---|---|---|---|---|
| Quality test | Immediately after preparation | Properties (appearance) | Homogeneous and smooth gel | Homogeneous and fragile gel | Sol with flowability |
| | | Water separation rate (%) | <1% | 12% | <1% |
| | | Pressing force through tube (N) | 36N | 30N | 56N |
| | | Suitability of discharge through tube | Easily dischargable with hand | Easily dischargable with hand | Strong force was needed for discharge with hand |
| Long-term storage test | After storage at 25° C. for 6 months | Properties (appearance) | Little water separated gel | Largely water separated gel | Partially water separated sol |
| | | Water separation rate (%) | 1.6% | 20.5% | 4.2% |
| | After storage at 25° C. for 12 months | Properties (appearance) | Slightly water separated gel | Largely water separated gel | Partially water separated sol |
| | | Water separation rate (%) | 2.8% | 28.1% | 10.4% |
| Vibration/drop test | After vibration/drop | Properties (appearance) | Maintained gel | Gel was disintegrated. Large water separation | Sol with flowability |
| | | Water separation rate (%) | 2.6% | 21.5% | <1% |
| Disintegration/ elution test using artificial gastric juice and artificial intestinal juice | First solution (artificial gastric juice) | Appearance of additive | Gel-like mass was formed and maintained | Disintegrated without forming mass | Flowable mass was formed |
| | | Solid remaining ratio (%) | 91% | 61% | 92% |
| | Second solution (artificial intestinal juice) | Appearance of additive | Mass was gradually disintegrated | Disintegrated without forming mass | Rapidly dissolved |
| | | Solid remaining ratio (%) | 42% | 45% | <10% |
| Gastric gel formation/holding test using rat | 30 min. after Administration | Shape of stomach content | Gel-like mass was formed and maintained | Fragile mass was formed and maintained | Flowable mass was formed |
| | | Solid remaining ratio (%) | 69% | 58% | 53% |

As shown in Table 2, the enteral nutrient of Comparative Example 1 prepared using the conventional technology showed a water separation rate of 10% or more even though the nutrient immediately after preparation was used. Moreover, the water separation rate increased to 20% or more when the enteral nutrient was stored for a long period of time. The enteral nutrient of Comparative Example 1 showed significant separation of water in the vibration/drop test. This may give rise to problems during usual distribution of the product. In the elution test, the solid remained in the first solution (pH: 1.2) corresponding to artificial gastric juice to some extent. However, disaggregated state of the solid was observed due to poor form-maintaining capability. The enteral nutrient of Comparative Example 2 exhibited a property difficult to discharge the nutrient by pressing the pouch by the hand due to high pressing force for passing through the tube. Further the enteral nutrient of Comparative Example 2 showed a property close to sol-form with decreasing in the form-maintaining capability thereof during storage. In the elution test, the solid nicely remained in the first solution (pH: 1.2) corresponding to artificial gastric juice. However, the solid was rapidly dissolved in the second solution (pH: 6.8) corresponding to artificial intestinal juice. Therefore, the risk that the solubility of the solid may change to a large extent depending upon the pH change in stomach due to the reflux of intestinal juice or the like was confirmed. The gel-type enteral nutrient according to the present invention obtained in Example 1 showed separation of water to only a small extent (3% or less) from immediately after preparation, and a pressing force for passing through the tube of 40 N or less possible to easily discharge by hand. In the long-term storage test, controversial increase in water separation rate was not observed (5% or less). The controversial separation of water was not occurred even in the vibration/drop test. It is considered that no problem occurs during distribution of the product. Moreover, in the elution test, the solid sufficiently remained in the first solution (pH: 1.2) corresponding to artificial gastric juice. The solid was not rapidly dissolve in the second solution (pH: 6.8) corresponding to artificial intestinal juice, remained as-is to some extent, and was intended to gradually disintegrate. It is considered that the solubility of the solid does not change to a large extent even if pH change occurs in stomach, and the risk of gastro-esophageal reflux may be minimal.

EXAMPLE 2

An enteral nutrient according to the present invention with a solid content of 1.5 kcal/g was prepared by adding the nutritional components in the ratio thereof shown in Table 3. The gel-type enteral nutrient according to the present invention to which agar and alginic acids were added was prepared in the same manner as in Example 1, except that the addition amount of water was changed. 200 g of the enteral nutrient was filled in an aluminum pouch, and subjected to retort sterilization at 121° C. for 15 minutes, thereby obtaining a product.

Comparative Example 3

An nutrient with a solid content of 1.5 kcal/g to which only agar was added was prepared by blending the nutritional components in the ratio thereof shown in Table 3 in accordance with the method described in patent documents 1 and 2. Specifically, the nutrient was prepared in the same manner as in Example 2, except that only agar solution was added but alginic acid and sodium alginic acid solution was not added.

Comparative Example 4

An nutrient with a solid content of 1.5 kcal/g to which only alginic acid was added was prepared by blending the nutritional components in the ratio thereof shown in Table 3. Specifically, the nutrient was prepared in the same manner as in Example 2, except that only the alginic acid and sodium alginic acid solution was added but the agar solution was not added.

TABLE 3

| Component | Blending amount | | |
|---|---|---|---|
| | Example 2 | Comparative Example 3 | Comparative Example 4 |
| Dextrin | 24.24 g | 24.24 g | 24.24 g |
| Soybean protein isolate | 2.50 g | 2.50 g | 2.50 g |
| Milk casein | 5.10 g | 5.10 g | 5.10 g |
| Fat (containing emulsifying agent) | 3.35 g | 3.35 g | 3.35 g |
| Calcium chloride | 176.4 mg | 176.4 mg | 176.4 mg |
| Calcium citrate | 59.3 mg | 59.3 mg | 59.3 mg |
| Magnesium chloride | 233.3 mg | 233.3 mg | 233.3 mg |
| Other minerals | 716.7 mg | 716.7 mg | 716.7 mg |
| Vitamins | 57.8 mg | 57.8 mg | 57.8 mg |
| Agar | 0.10 g | 0.50 g | — |
| Alginic acid | 0.04 g | — | 0.25 g |
| Sodium alginate | 0.04 g | — | 0.25 g |
| Water | 63.4 g | 63.1 g | 63.1 g |
| Total | 100 g | 100 g | 100 g |

Test Example 2

Regarding the enteral nutrient preparations of Example 2 and Comparative Examples 3 and 4, a quality test, a long-term storage test, a vibration/drop test, a disintegration/elution test using artificial gastric juice and artificial intestinal juice, and a gastric gel formation/holding test using a rat were conducted and compared.

The results are shown in Table 4.

TABLE 4

| Test | Sample | Evaluation item | Result | | |
|---|---|---|---|---|---|
| | | | Example 2 | Comparative Example 3 | Comparative Example 4 |
| Quality test | Immediately after preparation | Properties (appearance) | Homogeneous and smooth gel | Homogeneous and fragile gel | Slightly flowable gel |
| | | Water separation rate (%) | <1% | 5.0% | 1.8% |
| | | Pressing force through tube (N) | 34N | 51N | 40N |
| | | Suitability of discharge through tube | Easily dischargable with hand | Strong force was needed for discharge with hand | Dischargable with hand |
| Long-term storage test | After storage at 25° C. for 6 months | Properties (appearance) | Little water separated gel | Largely water separated gel | Slightly flowable gel |
| | | Water separation rate (%) | 1.2% | 7.8% | 2.2% |
| | After storage at 25° C. for 12 months | Properties (appearance) | Slightly water separated gel | Largely water separated gel | Slightly flowable and water separated gel |
| | | Water separation rate (%) | 2.1% | 10.3% | 60.4% |
| Vibration/drop test | After vibration/drop | Properties (appearance) | Maintained gel | Gel was disintegrated. Large water separation | Gel was disintegrated. Little water separation |
| | | Water separation rate (%) | 2.2% | 12.5% | 2.8% |
| Disintegration/ elution test using artificial gastric juice and artificial intestinal juice | First solution (artificial gastric juice) | Appearance of additive | Gel-like mass was formed and maintained | Disintegrated without forming mass | Flowable mass was formed |
| | | Solid remaining ratio (%) | 86% | 65% | 85% |
| | Second solution (artificial intestinal juice) | Appearance of additive | Mass was gradually disintegrated | Disintegrated without forming mass | Mass was gradually disintegrated |
| | | Solid remaining ratio (%) | 32% | 41% | <10% |
| Gastric gel formation/holding test using rat | 30 min. after administration | Shape of stomach content | Gel-like mass was formed and maintained | Fragile mass was formed and maintained | Flowable mass was formed |
| | | Solid remaining ratio (%) | 78% | 61% | 73% |

As shown in Table 4, the enteral nutrient of Comparative Example 3 prepared using the conventional technology showed a water separation rate of 5% or more as well as Comparative Example 1 even though it was a product immediately after preparation. A large pressing force (50 N or more) was required to discharge the enteral nutrient through the tube. Moreover, the water separation rate increased when the enteral nutrient was stored for a long period of time. The enteral nutrient of Comparative Example 3 showed an increase in separation of water was also confirmed in the vibration/drop test, therefore, it was thought that any problem might be occurred during distribution of the product. In the elution test, the solid nicely remained in the first solution (pH: 1.2) corresponding to artificial gastric juice to some extent. However, disaggregated state of the solid was observed due to form-maintaining capability. The enteral nutrient of Comparative Example 4 had not no trouble on the pressing force through a tube (40 N or less). However, the form-maintaining capability of the enteral nutrient decreased during long-term storage, the enteral nutrient changed so as to have flowability. In the elution test, the solid remained in the first solution (pH: 1.2) corresponding to artificial gastric juice. However, the solid was rapidly dissolved in the second solution (pH: 6.8) corresponding to artificial intestinal juice. Therefore, the risk that the solubility of the solid may change to a large extent depending upon the pH change in stomach due to the reflux of intestinal juice, for example. On the other hand, the gel-type enteral nutrient according to the present invention obtained in Example 2 showed separation of water to only a small extent (3% or less) from immediately after preparation, and the controversial increase in water separation rate was not also confirmed in the long-term storage test (5% or less). The controversial separation of water was occurred even in the vibration/drop test. It is considered that no problem occurs during distribution of the product. Moreover, in the elution test, the solid sufficiently remained in the first solution (pH: 1.2) corresponding to artificial gastric juice. The solid was not rapidly dissolved in the second solution (pH: 6.8) corresponding to artificial intestinal juice, but intended to remain as-is to a certain extent. It is considered that the solubility of the solid does not change to a large extent even if pH change occurs in stomach, and risk of gastro-esophageal reflux may be minimal.

Comparative Example 5

A nutrient with a solid content of 1.0 kcal/g to which agar and gelatin was added was prepared by blending the nutritional components in the ratio thereof shown in Table 5 in accordance with the method described in Patent Documents 1 and 2. Specifically, the nutrient was prepared in the same manner as in Example 1, except that only gelatin solution was added without adding the alginic acid solution to the agar solution.

Comparative Example 6

A nutrient with a solid content of 1.0 kcal/g to which agar and guar gum were added was prepared by blending the nutritional components in the amount thereof shown in Table 5 according to the method described in Patent Documents 1 and 2. Specifically, the nutrient was prepared in the same manner as in Example 1, except that only guar gum solution was added to agar solution without adding the alginic acid solution in Example 1.

Comparative Example 7

A nutrient with a solid content of 1.0 kcal/g to which a carrageenan and a guar gum were added was prepared by blending the nutritional components in the amount thereof shown in Table 5. Specifically, the enteral nutrient was prepared in the same manner as in Example 1, except that a carrageenan solution and a guar gum solution were added without adding the agar solution and the alginic acid solution in Example 1.

Comparative Example 8

A nutrient with a solid content of 1.0 kcal/g to which a carrageenan and alginic acid were added was prepared by blending the nutritional components in the amount thereof shown in Table 5. Specifically, the enteral nutrient was prepared in the same manner as in Example 1, except that an alginic acid solution was added to a carrageenan solution without adding the alginic acid solution to the agar solution in Example 1.

Comparative Example 9

A nutrient with a solid content of 1.0 kcal/g to which agar and alginic acid were added was prepare by blending the nutritional components (without soybean protein) in the amount thereof shown in Table 5 according to the method described in Patent Documents 1 and 2. Specifically, the enteral nutrient was prepared in the same manner as in Example 1, except that the soybean protein was not added.

TABLE 5

| | Blending amount | | | | | |
|---|---|---|---|---|---|---|
| Component | Example 1 | Comparative Example 5 | Comparative Example 6 | Comparative Example 7 | Comparative Example 8 | Comparative Example 9 |
| Combination of thickener and gelling agent | Agar Alginic acid | Agar Gelatin | Agar Guar gum | Carrageenan Guar gum | Carrageenan Alginic acid | Agar Alginic acid |
| Soybean protein | Used | Used | Used | Used | Used | Not used |
| Dextrin | 16.16 g | 16.16 g | 16.16 g | 16.16 g | 16.16 g | 16.16 g |
| Soybean protein isolate | 1.67 g | 1.67 g | 1.67 g | 1.67 g | 1.67 g | — |
| Milk casein | 3.40 g | 3.40 g | 3.40 g | 3.40 g | 3.40 g | 3.40 g |
| Fat (containing emulsifying agent) | 2.230 g | 2.230 g | 2.230 g | 2.230 g | 2.230 g | 2.230 g |
| Calcium chloride | 117.6 mg | 117.6 mg | 117.6 mg | 117.6 mg | 117.6 mg | 117.6 mg |
| Calcium citrate | 39.5 mg | 39.5 mg | 39.5 mg | 39.5 mg | 39.5 mg | 39.5 mg |
| Magnesium chloride | 155.5 mg | 155.5 mg | 155.5 mg | 155.5 mg | 155.5 mg | 155.5 mg |
| Other minerals | 477.8 mg | 477.8 mg | 477.8 mg | 477.8 mg | 477.8 mg | 477.8 mg |
| Vitamins | 38.5 mg | 38.5 mg | 38.5 mg | 38.5 mg | 38.5 mg | 38.5 mg |
| Agar | 0.25 g | 0.25 g | 0.25 g | | | 0.25 g |
| Alginic acid | 0.25 g | — | — | | 0.25 g | 0.25 g |
| gelatin | — | 1.6 g | — | | | |
| guar gum | — | — | 0.25 g | 0.25 g | | |
| Carrageenan | — | — | — | 0.25 g | 0.25 g | |
| Water | 75.2 g | 73.9 g | 75.2 g | 75.2 g | 75.2 g | 75.2 g |
| Total | 100 ml | 100 ml | 100 ml | 100 ml | 100 ml | 100 ml |

Test Example 3

Regarding the enteral nutrient preparations of Example 1 and Comparative Examples 5 to 9, a quality test, a long-term storage test, a vibration/drop test, and a disintegration/elution test using artificial gastric juice and artificial intestinal juice were conducted and compared. The results are shown in Table 6.

TABLE 6

| Test | Sample | Evaluation item | Example 1 | Comparative Example 5 | Comparative Example 6 |
|---|---|---|---|---|---|
| | | | Thickner, gelling agent, etc | | |
| | | | Agar, Alginic acid, With Soybean protein | Agar, Gelatin, With Soybean protein | Agar, Guar gum, With Soybean protein |
| Quality test | Immediately after preparation | Properties (appearance) | Homogeneous and smooth gel | Homogeneous and smooth gel | Homogeneous and fragile gel |
| | | Water separation rate (%) | <1% | <1% | 12.4% |
| | | Pressing force through tube (N) | 36N | 61N | 42N |
| | | Suitability of discharge through tube | Easily dischargable with hand | Strong force was needed for discharge with hand | Easily dischargable with hand |
| Long-term storage test | After storage at 25° C. for 6 months | Properties (appearance) | Little water separated gel | Little water separated gel | Largely water separated gel |
| | | Water separation rate (%) | 1.6% | 1.0% | 14.0% |
| Vibration/drop test | After vibration/drop | Properties (appearance) | Maintained gel | Maintained gel | Gel was disintegrated. Large water separation |
| | | Water separation rate (%) | 2.6% | 1.8% | 16.7% |
| Disintegration/elution test using artificial gastric juice and artificial intestinal juice | First solution (artificial gastric juice equivalent) | Appearance of additive | Gel-like mass was formed and maintained | Disintegrated without forming mass | Disintegrated without forming mass |
| | | Solid remaining ratio (%) | 91% | 45% | 49% |
| | Second solution (artificial intestinal juice equivalent) | Appearance of additive | Mass was gradually disintegrated | Disintegrated without forming mass | Disintegrated without forming mass |
| | | Solid remaining ratio (%) | 42% | 20% | 34% |

| Test | Sample | Evaluation item | Comparative Example 7 | Comparative Example 8 | Comparative Example 9 |
|---|---|---|---|---|---|
| | | | Thickner, gelling agent, etc | | |
| | | | Carrageenan, Guar gum, With Soybean protein | Carrageenan, Alginic acid, With Soybean protein | Agar, Alginic acid, Without Soybean protein |
| Quality test | Immediately after preparation | Properties (appearance) | Flowable sol | Homogeneous and smooth gel | Slightly uneven gel |
| | | Water separation rate (%) | 6.6% | 12% | 4.3% |
| | | Pressing force through tube (N) | 22N | 51N | 32N |
| | | Suitability of discharge through tube | Easily dischargable with hand | Strong force was needed for discharge with hand | Easily dischargable with hand |
| Long-term storage test | After storage at 25° C. for 6 months | Properties (appearance) | Largely water separated gel | Largely water separated gel | Slightly water separated gel |
| | | Water separation rate (%) | 18.7% | 10.5% | 5.2% |
| Vibration/drop test | After vibration/drop | Properties (appearance) | Gel was disintegrated. Large water separation | Gel was disintegrated. Little water separation | Gel was slightly disintegrated. Water separation |
| | | Water separation rate (%) | 11.6% | 6.7% | 9.8% |
| Disintegration/elution test using artificial gastric juice and artificial intestinal juice | First solution (artificial gastric juice equivalent) | Appearance of additive | Soft mass was formed and maintained | Gel-like mass was formed and maintained | Mass was gradually disintegrated |
| | | Solid remaining ratio (%) | 62% | 78% | 71% |
| | Second solution (artificial intestinal juice equivalent) | Appearance of additive | Rapidly dissolved | Rapidly dissolved | Mass was gradually disintegrated |
| | | Solid remaining ratio (%) | <10% | <10% | 25% |

As shown in Table 6, it is found that the combination (agar and gelatin) of Comparative Example 5 required a high pressing force through the tube and did not have gel form-maintaining capability in artificial gastric juice and artificial intestinal juice. Even when combining glucomannan or locust bean gum which was known to form elastic gel, the nutrient of Comparative Example 5 was not used due to the high pressing force through the tube. In Comparative Example 6 (agar and guar gum), a gel having large separation of water was formed, had a disadvantage even for its disintegration property in artificial gastric juice and artificial intestinal juice. So, guar gum could not improve the disadvantage of agar. Similar results were also obtained when combining crystalline cellulose or gum arabic. Comparative Example 7 (carrageenan and guar gum) is a representative example in which was thickeners and gelling agents other than agar and alginic acid were studied, the nutrient was not gelated, and was flowable. Comparative Example 8 (carrageenan and alginic acid) is a representative example in which alginic acid and a gelling agent other than agar were used. Alginic acid alone forms a gel with flowability (Comparative Example 4). A gel was formed when carrageenan was used in combination with alginic acid. However, a high pressing force through the tube was required, and separation of water occurred to a large extent. Although gelatin could be used for preparing a gel-type enteral nutrient by combining with gelling agent other than agar or alginic acid, however, it was not suitable for the intended gel-type enteral nutrient due to the high pressing force through the tube.

Taking both results shown in Table 6 and results obtained in the examples and comparative examples into consideration, according to the present invention obtained by combining agar and alginic acid can exert following four effect: (a) prevention of gastro-esophageal reflux after administration due to the excellent solid (gel) form-maintaining capability in a stomach, (b) capability easily passing through a feeding tube even though it is gel, (c) small change in shape and properties such as separation of water and the like during distribution and storage, and (d) capability to provide the gel-type nutrient which can be subjected to retort sterilization.

Regarding addition of soybean protein and hydrolysate thereof in the present invention, the present invention achieves a synergistic effect by combining 3 components of agar, alginic acid, and a soybean protein as previously described that "since the soybean protein is modified by heating to form a gel per se, the soybean protein is thought to have a synergistic effect on the gelation of agar and alginic acid."

The synergistic effect obtained by addition of the soybean protein is clear from the comparison between Comparative Example 9 (soybean protein was not used) and Example 1 (soybean protein was used) shown in Tables 5 and 6. In Comparative Example 9 in which the soybean protein was not used, though somewhat effects might be obtained, minimal non-uniform unevenness was observed on appearance, and separation of water occurred to a small extent. The product of Comparative Example 9 was slightly weak against vibration and drop, and had properties to easily broke and easily separate water. The amounts of agar and alginic acid may be increased in order to solve these problems. However, such a measure increases the pressing force through the tube and thus makes tube administration difficult. In this way, when the soybean protein was not used, some trouble on long-term stability and vibration/drop resistance may be occurred during distribution. Moreover, the nutrient product became soft when contacting with artificial gastric juice and artificial intestinal juice. Therefore, it is found that optimum results may be brought by adding the soybean protein together with agar and alginic acid in order to ensure a sufficient quality of the gel-type enteral nutrient during long-term storage and obtain sufficient effect preventing gastro-esophageal reflux by maintaining the form of the gel-type enteral nutrient in a stomach.

The invention claimed is:

1. An enteral nutrient gel comprising:
   0.05 to 0.5 g/100 ml agar,
   0.02 to 0.5 g/100 ml alginic acid and/or a salt thereof,
   0.5 to 4.4 g/100 ml soybean protein or a hydrolysate thereof,
   30 to 100 mg/100 ml calcium,
   15 to 50 mg/100 ml magnesium, and
   dextrin;
   wherein the gel is prepared from a solid composition comprising:
   8 to 30 wt % protein of the solid composition,
   2 to 25 wt % fats of the solid composition, and
   40 to 70 wt % dextrin in the solid composition.

2. The enteral nutrient gel according to claim 1, wherein the enteral nutrient gel has 0.5 to 2 kcal/g.

3. A pouch of enteral nutrient gel comprising a soft bag or a pouch containing, the enteral nutrient gel according to claim 1.

4. The pouch of enteral nutrient gel according to claim 3, wherein the soft bag or the pouch is an aluminum pouch.

5. The enteral nutrient gel according to claim 1, further comprising at least one of an oligosaccharide, a disaccharide and/or a monosaccharide.

* * * * *